United States Patent [19]

Galli et al.

[11] 4,285,969

[45] Aug. 25, 1981

[54] PYRETHROIDS

[75] Inventors: Remo Galli, Dresano; Franco Gozzo, San Donato Milanese; Ottorino Palla, Crema; Angelo Longoni, Milan, all of Italy

[73] Assignee: Montedison S.p.A., Milan, Italy

[21] Appl. No.: 127,118

[22] Filed: Mar. 4, 1980

[30] Foreign Application Priority Data

Mar. 9, 1979 [IT] Italy .................................. 20853 A/79

[51] Int. Cl.$^3$ ...................... A01N 53/00; C07C 61/35; C07C 69/743; C07C 121/75
[52] U.S. Cl. ............................... 424/304; 260/465 D; 260/544L; 560/124; 562/506; 424/305
[58] Field of Search ....................... 260/465 D, 544 L; 560/124; 424/304, 305; 562/506

[56] References Cited

U.S. PATENT DOCUMENTS 4,200,644 4/1980 Engel ............................... 260/465 D Primary Examiner—Dolph H. Torrence
Attorney, Agent, or Firm—Morgan, Finnegan, Pine, Foley & Lee

[57] ABSTRACT

The present invention concerns new pyrethroids having a high insecticidal activity. More particularly, this invention relates to novel esters of 2,2-dimethyl-cyclopropanecarboxylic acids substituted in the 3 position; the preparation of said novel esters; the use of said novel esters as insecticides and to insecticidal compositions containing said novel esters as the active ingredient. The present invention also includes providing intermediates for the synthesis of the new pyrethroids and the process for the preparation of said intermediates.

19 Claims, No Drawings

PYRETHROIDS

BACKGROUND OF THE INVENTION

Research for new pyrethroids is motivated by the fact that pyrethrum [a mixture of esters of crysanthemic acid (2,2-dimethyl-3-isobutenyl-cyclopropanecarboxylic acid) with a retronolone (2-alkenyl-3-methyl-cyclopent-2-en-4-olone)] is an insecticide of a natural origin, having a high insecticidal activity. For example, pyrethrum provides fast and strong insecticidal action by contact on winged insects, and with a low toxicity on mammals by oral administration, combined with a negligible dermal toxicity. However, the particular structure of the molecule renders pyrethrum easily degradable under atmospheric agents and, thus, it has no persistent action, a characteristic that does not allow its use in the protection of agricultural cultivations, limiting its use solely to domestic environments.

Research was thus oriented towards the synthesis of new compounds that, recalling the structure of pyrethrum, maintain its positive characteristics such as the high insecticidal activity and the low toxicity for mammals, while at the same time they are more resistant to the action of atmospheric agents.

There have been prepared numerous synthetic pyrethroids some of which displayed interesting characteristics [see for instance "Synthetic Pyrethroids" (by M. Elliot Ed.), ACS Symposium Series No. 42, Washington 1977].

Recently, in German Patent Application DOS No. 2730515 (Bayer), Phenoxy-benzyl cyclopropanecarboxylic esters substituted in position 3 of the cyclopropane ring by a vinyl group in its turn substituted by a halogen atom and by an optionally substituted phenyl-thio group, have been described.

OBJECTS OF THE INVENTION

An object of this invention is to provide novel pyrethroids having high insecticidal activity and low toxicity for mammals, while at the same time having a good resistance to the action of atmospheric agents. Another object of this invention is to provide a method for the preparation of the aforementioned pyrethroids.

Other objects of this invention are to provide novel intermediates, and their method of preparation, for use in the preparation of the novel pyrethroids referred to in the earlier mentioned objects.

Another object of the invention is to provide novel insecticidal compositions containing the novel pyrethroids as active ingredients and a method for combatting insects using the novel pyrethroids as insecticidal agents.

Further objects of the invention will be apparent from the discussion which follows.

SUMMARY OF THE INVENTION

Compounds having the formula:

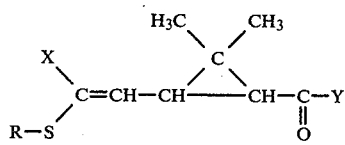

wherein:

R=alkyl optionally substituted, a heterocyclic aromatic group, CN, a substituted allyl, a substituted propargyl X=halogen Y=OH, halogen, OR' (R'=alkyl, benzyl), OR'';

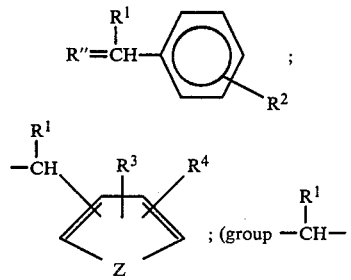

is linked to the heterocyclic ring in position 2 or 3)

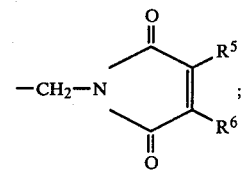

wherein:
$R^1$=H, CN, C≡CH
$R^2$=3-phenoxy, 3-benzyl, 4-allyl, 4-propargyl;
$R^3$=H, alkyl linked to the heterocyclic ring in position 3 or 2;
$R^4$=(in position 4 or 5 of the heterocyclic ring)=-benzyl, benzoyl, phenoxy, allyl, propargyl;
Z=O, S;
$R^5$ and $R^6$=alkyl $C_1$-$C_3$; or $R^5$ and $R^6$ together form an orthocondensed aromatic, heteroaromatic or aliphatic, saturated or unsaturated ring.

Compounds of formula I in which Y=OR'' are endowed with a high insecticidal activity, compounds of formula I in which Y=OH, halogen, OR' are intermediates for the synthesis of the insecticidal compounds. The preparation of the compounds of formula I is achieved by reacting a dihalomethyl sulphide of formula R—S—CHXX' (wherein R and X have the meanings indicated in formula I and X'=Cl, Br) in the presence of triphenylphosphine and a strong base with an ester of caronic aldehyde of formula:

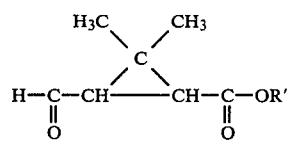

(wherein R' has the meanings indicated in formula I) obtaining thereby the compounds of formula I, in which Y=OR', and from which, by hydrolysis, are obtained the compounds of formula I in which Y=OH, these are then transformed into the corresponding acylic halides (Y=halogen) which are then made to react in the presence of a base with an alcohol of formula R''—OH (wherein R'' has the meanings indicated in formula I) thus obtaining the compounds of formula 1 in which Y=OR'.

GENERAL DESCRIPTION OF THE INVENTION

It has been found that an object of this invention may be realized by forming the compounds of formula I. The compounds of formula I may be prepared by reacting a dihalomethyl sulphide of formula: R—S—CHXX' (A) (wherein R and H have the meaning previously indicated and X'=Cl or Br) with an ester of caronic aldehyde (B) in the presence of triphenylphosphine (in a quantity equimolar with respect to the caronic aldehyde) and of a strong base, according to the following reaction:

$$R-S-CHXX' + H-\underset{\underset{O}{\|}}{C}-CH\underset{\underset{H_3C}{\diagdown}\underset{C}{\diagup}\underset{CH_3}{\diagup}}{-}CH-\underset{\underset{O}{\|}}{C}-OR' + (C_6H_5)_3P$$

(A) (B)

$$\downarrow -HX' \text{ |base}$$

$$R-S-\underset{X}{\underset{|}{C}}=CH-CH\underset{\underset{H_3C}{\diagdown}\underset{C}{\diagup}\underset{CH_3}{\diagup}}{-}CH-\underset{\underset{O}{\|}}{C}-OR' + (C_6H_5)_3P=O$$

The above-indicated reaction may conveniently be carried out by using the phase transfer method.

According to that technique, the sulphide, the aldehyde and the triphenylphosphine are dissolved in or admixed to an inert water immiscible solvent, to which is then added a small quantity of quaternary ammonium salt and an aqueous solution of an alkaline base. The whole mixture is then vigorously stirred. The reaction in general is exothermic and it is necessary to refrigerate externally the reaction vessel in order to maintain the temperature at values preferably not exceeding 50° C.

Once the reaction has been completed and the mixture brought down to room temperature, the two phases are separated and from the organic phase, operating according to standard laboratory procedures, the solvent is then removed and the triphenylphosphine oxide and possible impurities are separated, thus isolating the compound of general formula I wherein Y is equal to OR'.

From this compound, by standard hydrolysis reactions is then prepared the free acid (I, Y=OH) from which in its turn there is prepared the corresponding acylic halide (I, Y=halogen). Finally from the acylic halide, by reaction with an alcohol of formula R"—OH (wherein R" has the meanings previously indicated) the esters of formula I in which Y=OR" are obtained.

The dihalomethyl sulphides of formula R—S—CHXX' (Compound A, preceding reaction) are prepared easily by halogenation of the corresponding methylsulphides (R—S—CH$_3$) or of the corresponding thiolformates $$(R-S-\underset{\underset{O}{\|}}{C}-H).$$

The alkyl esters of caronic aldehyde (compound B, previous reaction) are known compounds both in the cis as well as in the trans form.

The pyrethroid compounds of this invention as well as the acids and intermediate esters, are in general isomeric mixtures due to the presence in the molecule of a double bond, of the cylopropyl ring and of asymmetric carbon atoms.

The possibility of starting from a caronic aldehyde already in the cis or trans form, allows to obtain the compounds of formula I exclusively in one of the two forms.

The pyrethroid compounds of this invention exhibit strong insecticide activity against a great number of insect species.

This strong insecticide activity is particularly effective against Musca domestica, Blatta orientalis and Locusta migratoria.

In the following Table 1 there is reported the insecticide activity of compounds according to this invention against some insect species compared with the activity of a known pyrethroid, Permethrin [3-phenoxybenzyl ester of 2,2-dimethyl-3-($\beta,\beta$-dichlorovinyl)-cyclopropanecarboxylic acid].

The pyrethroid compounds of this invention possess a good persistence of action and with a low toxicity towards warm-blooded animals.

TABLE 1

Insecticide activity at the indicated doses, expressed as mortality percentage.

| Insect specie | dose | Compound[1] A | B | R |
|---|---|---|---|---|
| Macrosiphum e. | 0.01 | 100 | | 100 |
| dose (°/$_{oo}$) | 0.001 | 95 | | 38 |
| Leptinotarsa d. | 0.05 | 100 | 100 | 100 |
| dose (°/$_{oo}$) | 0.01 | | 100 | |
| Musca d. | 0.05 | 100 | | 100 |
| (topical application) | 0.01 | 100 | 100 | 70 |
| dose ($\delta$/ins.) | 0.005 | 80 | | 20 |
| | 0.0025 | | 80 | |
| Blatta o. | 0.01 | 100 | | 75 |
| dose (g/m$^2$) | 0.005 | 100 | | 35 |
| | 0.001 | 90 | | |
| Locusta m. | 0.05 | 100 | | 0 |
| dose (°/$_{oo}$) | | | | |

Notes to Table 1
[1]Compound A = α-cyano-3-phenoxybenzyl ester of (±)-trans-2,2-dimethyl-3-($\beta$-chloro-$\beta$- methylthio-E,Z-vinyl)-cyclopropanecarboxylic acid (see Example 3).
Compound B = α-cyano-3-phenoxy-benzyl ester of (±)-cis-2,2-dimethyl-3-($\beta$-chloro-$\beta$-methylthio-E,Z-vinyl)-cyclopropanecarboxylic acid (see Example 5).
Compound R = Permethrin [Reference compound]

The insecticide compounds of general formula I (in which Y=OR") may be applied to a zone where insect control is desired both as technical materials or as suitable compositions or formulations.

Suitable compositions comprise an insecticide compound of formula I as active ingredient in combination with one or more suitable inert carriers and/or surface active agents, and optionally other active compounds such as other insecticides, acaricides, nematocides etc.

Suitable formulations include granules, dusts, wettable powders, emulsifiable concentrates, solutions, dispersions and the like.

The active ingredient may be present in a suitable composition at a concentration of from 0.1% to 99% by weight.

While the application rate of the formulations varies widely depending on the type of formulation, the active compound, the mode of application and the environment, an effective insecticidal amount of the active principle must be applied and the practical rate may vary in the range of 0.01 to 3 Kg/hectare.

SPECIFIC DESCRIPTION OF THE INVENTION

In order to even further illustrate this invention, in the following are given a number of examples.

EXAMPLE 1

Preparation of ethyl ester of (±)-trans-2,2-dimethyl-3-(β-chloro-β-methylthio-E,Z-vinyl)-cyclopropanecarboxylic acid To a mixture of:
2.7 g (0.016 mols) of trans-caronic aldehyde (ethyl ester),
3.2 g (0.02 mols) of 1,1-dichloro-dimethylsulphide ($CH_3$—S—$CHCl_2$),
0.2 g of triethyl-benzyl-ammoniumchloride,
4.3 g (0.016 mols) of triphenylphosphine,
20 ml benzene,
were admixed, under vigorous stirring, 6 ml of an aqueous solution of 50% NaOH.

The reaction proved exothermic and the temperature was allowed to rise slowly up to 40° C. in 15 minutes; after which it was refrigerated externally by means of a cooling bath, maintaining the temperature at 40° C. for about 4-5 minutes. Thereupon the mixture was allowed to cool down to room temperature. Then there were added 40 ml of benzene and 20 ml of water. The organic phase was separated, anhydrified with anhydrous $Na_2SO_4$ and then was filtered. The solvent was removed under vacuum and the residue (thick oil, 8.7 g) was diluted with ethyl ether (50-60 ml). Then there was separated the triphenylphosphine oxide which was then removed by filtering. The etheral solution, to which had been added 20 ml of n.hexane, was allowed to percolate through a 5 cm layer of silicon gel, in order to eliminate the tarry residues, whereafter the solvent was removed under vacuum.

Thereby were obtained 3.1 g of the desired product. (The elementary analysis proved consistent with the assigned structure).

IR (Infrared absorption spectrum): 1725 $cm^{-1}$ ($\nu$C=O); 1175 $cm^{-1}$ ($\nu$C—O—C).

There was absence of absorption bands in the zone of the aldehyde group.

EXAMPLE 2

Preparation of (±)-trans-2,2-dimethyl-3-(β-chloro-β-methylthio-E,Z-vinyl)-cyclopropanecarboxylic acid and of the corresponding acyl chloride To a solution of the ethyl ester obtained as described in example 1 (1.3 g) in 15 ml of absolute methanol, there was added, under stirring, 1 g of solid KOH. Once the addition has been completed the solution was reflux heated for 2 hours. Thereupon the solution was allowed to cool down, the solvent was then evaporated and to the residue were added 5 ml of water and 20 ml of diethylether. Thereupon the aqueous phase was separated and acidified with concentrated HCl and then extracted with ethyl ether. From the ethereal phase there was then removed the solvent, thereby obtaining 0.8 g of the desired product in the form of an oil.

IR: 1690 $cm^{-1}$ ($\nu$C=O).

By treating the acid thus obtained with $SOCl_2$, there were obtained 0.9 g of the corresponding acylic chloride.

IR = 1770 $cm^{-1}$ ($\nu$C=O).

EXAMPLE 3

Preparation of the alpha-cyano-3-phenoxybenzyl ester of (±)-trans-2,2-dimethyl-3-(β-chloro-β-methylthio-E,Z-vinyl)-cyclopropanecarboxylic acid To a solution of 0.9 g of the corresponding acylic chloride, prepared as described in example 2, in 15 ml of anhydrous ethyl ether, was added, at 0°–5° C. a solution of 0.8 g of α-cyano-3-phenoxybenzyl alcohol in 5 ml of anhydrous ether. This reaction mixture was then stirred at 0°–5° C. for 1 hour.

The reaction mixture was then left to rest overnight at room temperature, whereafter the pyridinium hydrochlorate that had formed was filtered and the solvent removed under vacuum.

There were obtained 2 g of a raw product which was chromatographed on silica gel (length of column: 20 cm, diam. 4 cm, eluent: n.hexane-ethyl acetate in a ratio of 4:1). In this way was obtained 1 g of the desired product (purity greater than 94% GLC).

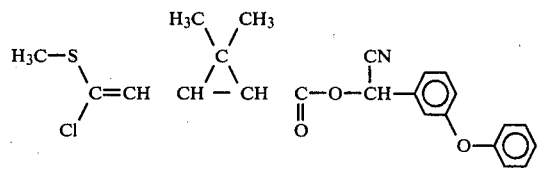

Elemental analysis: Theoretical C=64.55%; Found: C=64.02%; Theoretical H=5.18%; Found H=5.18%; Theoretical N=3.27%; Found: N=3.13%.

IR: 1730 $cm^{-1}$ ($\nu$C=O), 1580 and 1480 $cm^{-1}$ ($\nu$aromatic); 1240 $cm^{-1}$ ($\nu$C—O—C), 1140 $cm^{-1}$ ($\nu$C—O—C).

$^1$H NMR (nuclear magnetic resonance) ($CDCl_3$, TMS): $\delta$=2,3 ppm (3H, $SCH_3$); =5,65 ppm (1H, HC=); =6,4 ppm (1H, CH—CN).

EXAMPLE 4

Preparation of the ethyl ester of (±)-cis-2,2-dimethyl-3-(β-chloro-β-methylthio-E,Z-vinyl)-cyclopropane-carboxylic acid A mixture consisting of:
5.2 g (0.04 moles) of 1,1-dichloro-dimethylsulphide,
10 g (0.038 moles) of triphenylphosphine
50 ml of benzene
0.4 g of triethyl-benzyl-ammonium chloride
11 ml of an aqueous NaOH solution at 50% concentration was vigorously stirred for 5 minutes at room temperature and then for 10 minutes at 35° C.

The reaction mixture became deep orange coloured. Stirring was interrupted and 3.4 g (0.02 moles) of cis-caronic aldehyde (ethyl ester) were added to the reaction mixture which was then left to stand at 35° C. for 10 minutes and at room temperature for 2 hours.

The organic layer was then separated, anhydrified with anhydrous $Na_2SO_4$ and filtered. The solvent was then evaporated obtaining as residue 7.3 g of an oil containing beside the desired product, unreacted triphenylphosphine and cis-caronicaldehyde. The desired product was purified by chromotography on a silica gel column (length=50 cm, diameter=4 cm, silica gel size 0.006–0.2 mm, eluent: n.hexane-ethylacetate 5:1 v/v).

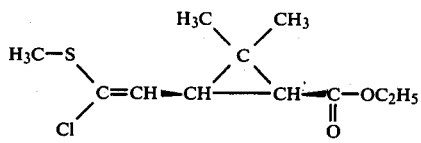

IR: 1730 cm$^{-1}$ ($\nu$C=O); 1190, 1142 cm$^{-1}$ ($\nu$ of the ester group); No absorption bands in the zone of the aldehyde group.

EXAMPLE 5

Preparation of α-cyano-3-phenoxybenzyl ester of (±)-cis-2,2-dimethyl-3-(β-chloro-β-methylthio-E,Z-vinyl)-cyclopropanecarboxylic acid The compound of Example 4 was converted into its corresponding acyl chloride by a procedure analogous to the one described in Example 2.

The acyl-chloride was then reacted with α-cyano-3-phenoxybenzyl alcohol, according to a procedure analogous to the one described in Example 3.

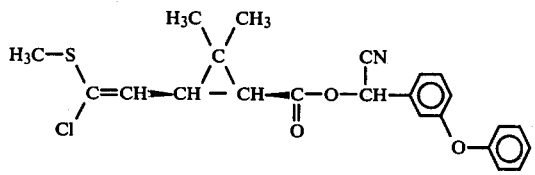

$^1$H NMR (CDCl$_3$, TMS); δ(ppm) 1.23 (6H, geminal methyl groups); 1.7–2.7 (2H, protons on the cyclopropane ring); 2.3 (3H, S—CH$_3$); 6.18 (1H, CH=); 6.3 (1H, CH—CN); 6.8–7.75 (9H, aromatic protons).

EXAMPLE 6

Preparation of the ethyl ester of (±)-trans-2,2-dimethyl-3-(β-bromo-β-methylthio-E,Z-vinyl)-cyclopropane carboxylic acid A mixture consisting of 2.2 g (0.01 moles) of 1,1-dibromo-dimethylsulphide (CH$_3$—S—CHBr$_2$)

1.7 g (0.01 moles) of trans-caronic aldehyde (ethyl ester)

2.6 g (0.01 moles) of triphenylphosphine 20 ml of benzene was heated in 2 hours up to 60° C. and kept 1 hour at this temperature.

The mixture was then cooled at room temperature and 0.2 g of triethylbenzyl-ammonium chloride and 6 ml of an aqueous NaOH solution at 50% concentration were added to it.

The temperature of the resulting mixture rose spontaneously up to 45° C.

Once the exothermic reaction ceased, the organic phase was separated and percolated through a silica gel column (4 cm height, eluent diethyl-ether).

The solvent was evaporated and the residue (2.1 g of an oil) analyzed by gas-chromatography proved to contain, beside the desired product, unreacted triphenylphosphine and caronic aldehyde.

The residue was chromatographed on a silica gel column (height 30 cm, diameter 4 cm, silica gel size 0.006–0.2 mm, eluent n.hexane-ethyl acelate 5:1 v/v) thereby obtaining 0.3 g of the desired product

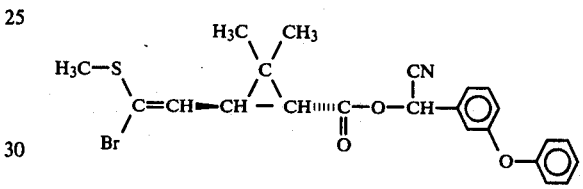

MS (Mass spectroscopic data): M$^+$=292, 294; M$^+$—CH$_3$=277, 279.

$^1$H—NMR (CDCl$_3$, TMS): δ(ppm) 1.3 (9H, geminal methyl groups and CH$_3$—CH$_2$); 1.6 (d, 1H, H$_B$); 2.2 (m, 1H, H$_A$); 2.33 (s, 3H, SCH$_3$); 4.13 (q, 2H, CH$_2$—CH$_3$); 5.93 (d, 1H, CH=); s=singlet, d=doublet, q=quartet, m=multiplet.

EXAMPLE 7

Preparation of α-cyano-3-phenoxybenzyl ester of (±)-trans-2,2-dimethyl-3-(β-bromo-β-methylthio-E,Z-vinyl)-cyclopropane carboxylic acid The compound was prepared starting from the ethyl ester of Example 6 and by a procedure analogous to the one described in Example 5.

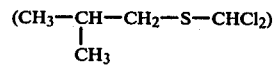

IR 1735 cm$^{-1}$ ($\nu$C=O); 1480 and 1580 cm$^{-1}$ ($\nu$ aromatic groups); 1235 and 1140 cm$^{-1}$ ($\nu$C—O—C).

NMR (CDCl$_3$, TMS): δ(ppm) 2.33 (s, 3H, SCH$_3$); 5.9 (d, 1H, CH=); 6.4 (1H, CH—CN); s=singlet, d=doublet.

EXAMPLE 8

Preparation of ethyl ester of (±)-trans-2,2-dimethyl-3-[β-chloro-β-(2-methyl)propylthio-E,Z-vinyl]-cyclopropanecarboxylic acid The compound was prepared starting from trans-caronic aldehyde (ethyl ester) and trichloromethyl-isobutyl-sulphide (CH$_3$—CH—CH$_2$—S—CHCl$_2$)
  |
  CH$_3$ by operating according to a procedure analogous to the one described in example 1.

The reaction proved not to be exothermic and heating was maintained at 45° C. for 1 hour after which the reaction mixture was worked-up as described in Example 1.

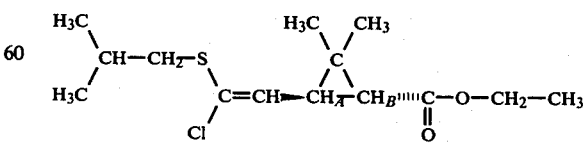

NMR (CDCl$_3$, TMS): δ(ppm): 0.95–1.5 (m, 15H, methyl groups); 1.6 (d, 1H, H$_B$); 2 (m, 1H, CH$_2$—CH); 2.33 (dxd, 1H, H$_A$); 2.65–2.70 (d,d, 2H, S—CH$_2$); 4.1 (q, 2H, O—CH$_2$); 5.70–5.75 (d,d, 1H, —CH=). d=dou-

EXAMPLE 9

Preparation of α-cyano-3-phenoxybenzyl ester of (±)-trans-2,2-dimethyl-3-[β-chloro-β-(2-methyl)-propylthio-E,Z-vinyl]-cyclopropanecarboxylic acid The compound was prepared starting from the ethyl ester of Example 8 and by operating as described in Example 5.

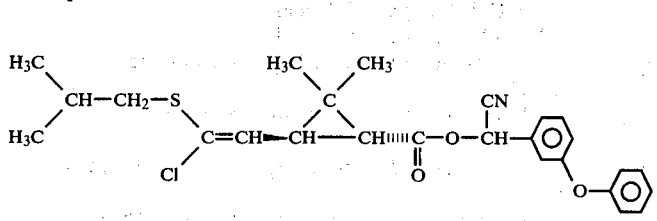

The NMR and IR spectroscopic data are consistent with the assigned structure.

EXAMPLE 10

Insecticide activity

Compounds according to the invention were tested on larvae and/or adults of the following phytophagus species by means of the following methodologies. (The mortality percentage has been calculated with respect to that of untreated insects).

(A) Biological activity on *Macrosiphum euphorbiae:* (afides)

Pot grown small potato plants were infested with adult females of the afide and, after a few hours, were besprinkled with an aqueous dispersion of the products under examination. The mortality percentage was determined after 24 hours from the treatment.

(B) Biological activity on *Leptinotarsa decemlineata:* (Coleoptera)

Pot grown small potato plants were infested with 4 days old larvae and then besprinkeled with an aqueous dispersion of the product under examination.

The mortality percentage was determined after 48 hours from the treatment.

(C) Biological activity on *Musca domestica:* (Diptera)

4-days old adults were treated by topical application by means of a microsyringe with an acetonic solution of the products under examination.

The mortality percentage was determined after 24 hours from the treatment.

(D) Biological activity on *Blatta orientalis:* (Orthoptera)

The bottom and walls of crystallizers of glass were treated uniformly with an acetonic solution of the products under examination.

After evaporation of the solvent in each crystallizer there were introduced neanides 80-100 days old, closing the crystallizers, thereupon, with a metal net lid.

After 24 hours from the start up of the treatment, the insects were transferred into similar, untreated crystallizers and were then suitably nurished.

The mortality percentage was determined 48 hours after the start of the treatment.

(E) Biological activity on *Locusta migratoria:* (Orthoptera)

Cut-off mais leaves were besprinkled with an aqueous dispersion of the products under examination. After drying, the leaves were administered as nurishment to 8-days old neanides of *Locusta migratoria.*

The mortality percentage was determined 72 hours after the treatment.

We claim:

1. Compounds of general formula:

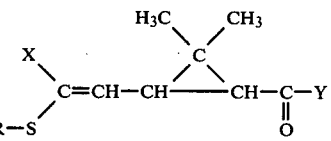

wherein:
R = $C_1$-$C_4$ alkyl
X = halogen
Y = OR'' and

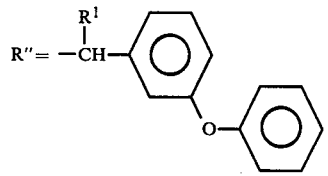

wherein $R^1$ = H or CN.

2. Compounds according to claim 1 in which X = Cl, Br.

3. Compounds according to claim 1 in which R = $CH_3$.

4. α-cyano-3-phenoxybenzyl ester of (±)-cis-2,2-dimethyl-3-(β-chloro-β-methylthio-E,Z-vinyl)-cyclopropane carboxylic acid.

5. α-cyano-3-phenoxybenzyl ester of (±)-trans-2,2-dimethyl-3-(β-chloro-β-methylthio-E,Z-vinyl)-cyclopropane carboxylic acid.

6. α-cyano-3-phenoxybenzyl ester of (±)-trans-2,2-dimethyl-3-(β-bromo-β-methylthio-E,Z-vinyl)-cyclopropane carboxylic acid.

7. Compounds according to claim 1 in which R = isobutyl.

8. α-cyano-3-phenoxybenzyl ester of (±)-trans-2,2-dimethyl-3-(β-chloro-β-isobutyl-E,Z-vinyl)-cyclopropane carboxylic acid.

9. Method for fighting infestations by insects characterized in that an effective insecticidal amount of one or more of the compounds of claim 1 are applied as such or in the form of suitable compositions on the zone in which insect control is desired.

10. The method of claim 9 in which a compound of claim 4 is applied on the zone in which insect control is desired.

11. The method of claim 9 in which a compound of claim 8 is applied on the zone in which insect control is desired.

12. Insecticidal compositions comprising an effective insecticidal amount of one or more of the compounds of claim 1 in combination with a suitable inert carrier.

13. Insecticidal compositions according to claim 12 in which the compound is a compound of claim 3.

14. Insecticidal compositions according to claim 12 in which the compound is a compound of claim 7.

15. Compounds having the general formula:

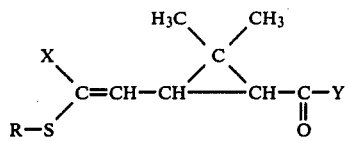

wherein:
R = $C_1$–$C_4$ alkyl
X = halogen
Y = OH, halogen, OR' and
R' = $C_1$–$C_4$ alkyl or benzyl.

16. Compounds according to claim 15, in which X = Cl, Br.

17. Compounds according to claim 15 in which Y = OH.

18. Compounds according to claim 15 in which Y = Cl.

19. Compounds according to claim 15 in which Y = OR' and R' = $C_1$–$C_4$ alkyl.

* * * * *